(12) United States Patent
McBride

(10) Patent No.: US 9,402,659 B2
(45) Date of Patent: Aug. 2, 2016

(54) SPINAL IMPLANT SYSTEM

(71) Applicant: Warsaw Orthopedic, Inc., Warsaw, IN (US)

(72) Inventor: Larry T. McBride, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 228 days.

(21) Appl. No.: 13/959,911

(22) Filed: Aug. 6, 2013

(65) Prior Publication Data
US 2015/0045834 A1    Feb. 12, 2015

(51) Int. Cl.
*A61B 17/70* (2006.01)

(52) U.S. Cl.
CPC ........... *A61B 17/7077* (2013.01); *A61B 17/708* (2013.01); *A61B 17/7089* (2013.01)

(58) Field of Classification Search
CPC ........... A61B 17/7082; A61B 17/8872; A61B 2017/681; A61B 17/025; A61B 17/7083; A61B 17/7086; A61B 17/7089; A61B 17/7077; A61B 17/708
USPC .......................................... 606/250–279, 99
See application file for complete search history.

(56) References Cited

U.S. PATENT DOCUMENTS

| | | | |
|---|---|---|---|
| 3,963,028 A | 6/1976 | Cooley et al. | |
| 5,336,170 A | 8/1994 | Salerno et al. | |
| 5,891,145 A | 4/1999 | Morrison et al. | |
| 6,530,929 B1 | 3/2003 | Justis et al. | |
| 7,008,422 B2 | 3/2006 | Foley et al. | |
| 7,011,660 B2 | 3/2006 | Sherman et al. | |
| 7,188,626 B2 | 3/2007 | Foley et al. | |
| 7,226,413 B2 | 6/2007 | McKinley | |
| 7,476,240 B2 | 1/2009 | Raymond et al. | |
| 7,491,218 B2 | 2/2009 | Landry et al. | |
| 7,563,264 B2 | 7/2009 | Landry et al. | |
| 7,575,581 B2 | 8/2009 | Lovell | |
| 7,666,189 B2 | 2/2010 | Gerber et al. | |
| 7,717,944 B2 | 5/2010 | Foley et al. | |
| 7,758,617 B2 | 7/2010 | Iott et al. | |
| 7,763,055 B2 | 7/2010 | Foley | |
| 7,794,464 B2 | 9/2010 | Bridwell et al. | |
| 7,802,547 B2 | 9/2010 | Inomoto et al. | |
| 7,842,044 B2 | 11/2010 | Runco et al. | |
| 7,846,093 B2 | 12/2010 | Gorek et al. | |
| 7,854,751 B2 | 12/2010 | Sicvol et al. | |
| 7,862,595 B2 | 1/2011 | Foley et al. | |

(Continued)

OTHER PUBLICATIONS

Kevin T. Foley, M.D., Medtronic Sofamor Danek, Horizon® Sextant™ Rod Insertion System Surgical Technique; Minimal Access Spinal Technologies ©2003 Medtronic Sofamor Danek, Inc.

*Primary Examiner* — Mary Hoffman
*Assistant Examiner* — Tara R Carter

(57) ABSTRACT

A surgical instrument comprises a first member including a first body connected to at least one second body. The first body is configured for disposal of an implant support having an outer surface. The at least one second body includes a capture element configured to dispose an implant support having an outer surface with the at least one second body such that the outer surfaces are spaced apart and each of the implant supports are engageable with a first implant. A second member is connected with the first member and is engageable with a second implant. The members are relatively movable to dispose the second implant with the implant supports and to align the second implant with at least one of the first implants. Systems and methods are disclosed.

19 Claims, 10 Drawing Sheets

(56) References Cited

U.S. PATENT DOCUMENTS

| | | |
|---|---|---|
| 7,867,259 B2 | 1/2011 | Foley et al. |
| 7,887,541 B2 | 2/2011 | Runco et al. |
| 7,914,558 B2 | 3/2011 | Landry et al. |
| 7,918,857 B2 | 4/2011 | Dziedzic et al. |
| 7,918,858 B2 | 4/2011 | Stad et al. |
| 7,922,746 B2 | 4/2011 | Miller |
| 7,927,334 B2 | 4/2011 | Miller et al. |
| 7,947,046 B2 | 5/2011 | Justis et al. |
| 7,985,242 B2 | 7/2011 | Forton et al. |
| 8,012,141 B2 | 9/2011 | Wright et al. |
| 8,096,996 B2 | 1/2012 | Gutierrez et al. |
| 8,105,362 B2 | 1/2012 | Duarte |
| 8,177,817 B2 | 5/2012 | Fallin |
| 8,246,624 B2 | 8/2012 | Forton et al. |
| 8,308,774 B2 | 11/2012 | Hoffman et al. |
| 2002/0058944 A1* | 5/2002 | Michelson ............... 606/79 |
| 2005/0006434 A1 | 1/2005 | Wales et al. |
| 2005/0131419 A1 | 6/2005 | McCord et al. |
| 2006/0074418 A1 | 4/2006 | Jackson |
| 2006/0079903 A1 | 4/2006 | Wong |
| 2006/0111712 A1 | 5/2006 | Jackson |
| 2006/0122597 A1 | 6/2006 | Jones et al. |
| 2006/0200135 A1 | 9/2006 | Sherman et al. |
| 2006/0229614 A1 | 10/2006 | Foley et al. |
| 2006/0293680 A1 | 12/2006 | Jackson |
| 2007/0027468 A1 | 2/2007 | Wales et al. |
| 2007/0049931 A1* | 3/2007 | Justis et al. ............... 606/61 |
| 2007/0213714 A1 | 9/2007 | Justis et al. |
| 2008/0015601 A1 | 1/2008 | Castro et al. |
| 2008/0172062 A1 | 7/2008 | Donahue et al. |
| 2008/0234678 A1 | 9/2008 | Gutierrez et al. |
| 2008/0243190 A1 | 10/2008 | Dziedzic et al. |
| 2008/0319477 A1* | 12/2008 | Justis et al. ............... 606/232 |
| 2009/0171391 A1 | 7/2009 | Hutton et al. |
| 2009/0222046 A1 | 9/2009 | Gorek |
| 2009/0228055 A1 | 9/2009 | Jackson |
| 2009/0228056 A1 | 9/2009 | Jackson |
| 2009/0234395 A1 | 9/2009 | Hoffman et al. |
| 2009/0318972 A1 | 12/2009 | Jackson |
| 2010/0036443 A1 | 2/2010 | Hutton et al. |
| 2010/0069972 A1 | 3/2010 | Jones et al. |
| 2010/0198271 A1 | 8/2010 | Leone |
| 2010/0218581 A1 | 9/2010 | Khowaylo et al. |
| 2010/0312279 A1 | 12/2010 | Gephart et al. |
| 2011/0015678 A1 | 1/2011 | Jackson |
| 2011/0022088 A1 | 1/2011 | Forton et al. |
| 2011/0106187 A1 | 5/2011 | Foley et al. |
| 2011/0125192 A1 | 5/2011 | Justis et al. |
| 2011/0202096 A1 | 8/2011 | White et al. |

\* cited by examiner

SPINAL IMPLANT SYSTEM

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, a surgical instrument is provided. The instrument comprises a first member including a first body connected to at least one second body. The first body is configured for disposal of an implant support having an outer surface. The at least one second body includes a capture element configured to dispose an implant support having an outer surface with the at least one second body such that the outer surfaces are spaced apart and each of the implant supports are engageable with a first implant. The instrument includes a second member connected with the first member that is engageable with a second implant. The members are relatively movable to dispose the second implant with the implant supports and to align the second implant with at least one of the first implants. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
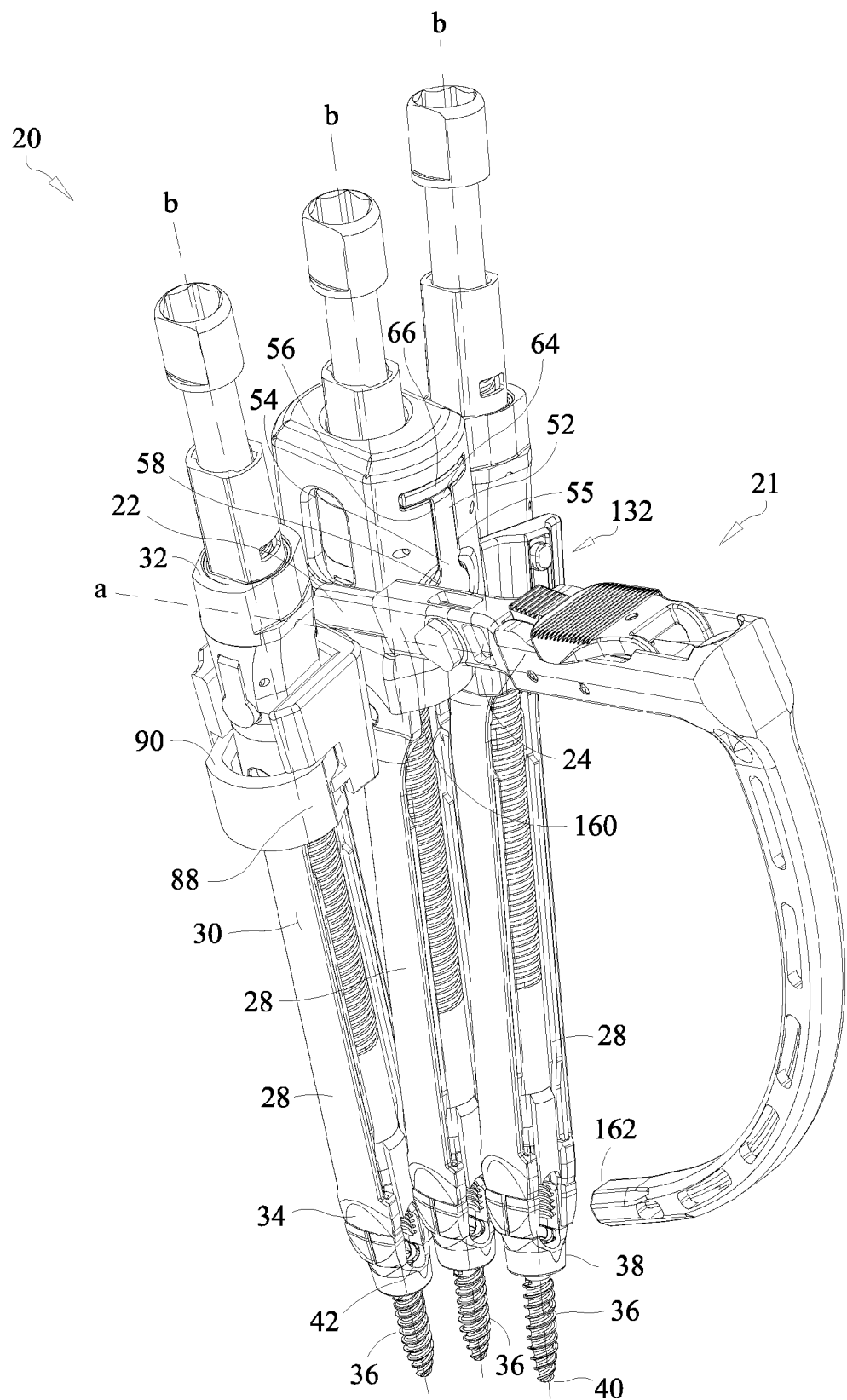
FIG. 1 is a perspective view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine.

In one embodiment, one or all of the components of the surgical system are disposable, peel-pack, pre-packed sterile devices used with an implant. One or all of the components of the surgical system may be reusable. The surgical system may be configured as a kit with multiple sized and configured components.

In one embodiment, the system includes a constrained minimally invasive rod insertion device that is used in percutaneous lateral fusion procedures. In various embodiments, extenders attach to the device such that the extenders are spaced apart and do not mate together.

In one embodiment, a method of mating extenders with the device for delivery of a spinal implant to a surgical site is provided. A first extender, a second extender and a third extender, each engageable with a bone fastener are provided. The device, comprising a first member and a second member is provided and a first body of the first member is lowered onto the second extender. The first body is disposed and connected centrally relative to at least one second body. The at least one second body includes a pair of second bodies, such as, for example, housings. The housings include trap doors that are unlocked and locked for disposal of the first and third extenders. The first extender is rotated and the trap door is unlocked and opened. The first extender is inserted into the housing and the trap door is closed until an audible click is provided, locking the extender into the housing. The third extender is rotated and locked into the housing in the same manner as the first extender. The device includes a lock comprising a safety latch and a lever. The safety latch is released and the lever is pulled in an upward direction to open a collet disposed at the proximal end of the second member. A spinal rod is inserted into the distal end of the second member and the lever is closed to lock the spinal rod in place.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-10, there is illustrated components of a surgical system, such as, for example, a spinal implant system 20 in accordance with the principles of the present disclosure.

The components of spinal implant system 20 can be fabricated from biologically acceptable materials suitable for medical applications, including metals, synthetic polymers, ceramics and bone material and/or their composites, depending on the particular application and/or preference of a medical practitioner. For example, the components of spinal implant system 20, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elastoplastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 20 may have material composites, including the above materials, to achieve various desired characteristics such as strength, rigidity, elasticity, compliance, biomechanical performance, durability and radiolucency or imaging preference. The components of spinal implant system 20, individually or collectively, may also be fabricated from a heterogeneous material such as a combination of two or more of the above-described materials. The components of spinal implant system 20 may be monolithically formed, integrally connected or include fastening elements and/or instruments, as described herein.

Spinal implant system 20 is employed, for example, with a minimally invasive procedure, including percutaneous techniques, mini-open and open surgical techniques to deliver and introduce an implant, such as, for example, a bone fastener, at a surgical site within a body of a patient, for example, a section of a spine. In some embodiments, spinal implant system 20 and related methods may be employed with treatments using minimally invasive and percutaneous techniques.

Spinal implant system 20 includes a spinal instrument 21 that includes a first member 22. Member 22 is configured for engagement with one or a plurality of implant supports and for adjustable engagement with a second member, as described herein. Member 22 includes a linear configuration and defines a longitudinal axis a. An end 24 is configured for engagement with the second member and an end 26 is configured for engagement with a first body and at least one second body that are configured for disposal of the implant supports, as described herein.

System 20 includes an implant support, such as, for example, an extender 28. Extender 28 is configured for engagement with member 22 via the first body and/or the at least one second body as described herein. Extender 28 defines a longitudinal axis b, and includes an outer surface 30 that extends between a proximal end 32 and a distal end 34. In some embodiments, surface 30 is at least partially smooth, rough or threaded. Distal end 34 is configured for engagement with one or a plurality of implants, such as, for example, bone fasteners 36. Each of bone fasteners 36 include a proximal portion, such as for example, a receiver 38 and a distal portion, such as for example, a shaft 40. Receiver 38 includes a pair of spaced apart walls that define an implant cavity 42. Cavity 42 is configured for engagement with a second implant, such as, for example, a spinal rod, described herein. In some embodiments, cavity 42 may be variously configured, including, for example, V-shaped, polygonal, or tapered depending upon the geometry of the spinal construct to be received within cavity 42.

Member 22 of instrument 21 includes a first body, such as, for example, a housing 44. Housing 44 is configured for disposal of extender 28. Housing 44 includes an interior surface 46 that defines a passage 48. Passage 48 engages outer surface 30 of extender 28. In some embodiments, passage 48 is smooth, rough or threaded to facilitate engagement with surface 30. In various embodiments, passage 48 is tubular. Housing 44 includes an exterior surface 50. In various embodiments, the shape of housing 44 is rectangular, square and/or tubular.

Housing 44 includes a lock 52. Lock 52 is configured for manipulation to releasably engage and disengage extender 28 from housing 44. Lock 52 includes a latch 54. Latch 54 is disposed within a recess 55 defined by surface 50. Latch 54 extends between a proximal end 56 and a distal end 58. In one embodiment, latch 54 includes an opening 60 and a pin 62 connects and facilitates movement of latch 54 within recess 55. Pin 62 is inserted into both an aperture 63 defined between surfaces 46, 50, and opening 60. In some embodiments, aperture 63 can be an opening, hole, slot, orifice or slit.

End 56 includes a prong 64 that engages a latch 66 disposed within a recess 68 of housing 44. In one embodiment, end 58 engages a biasing member, such as, for example, a spring 70. A button 72 is positioned on end 58. Button 72 is depressible and engages spring 70 causing prong 64 to engage latch 54 to either engage or disengage with surface 30 of extender 28 to either lock or unlock extender 28 within passage 48.

Figure 2:
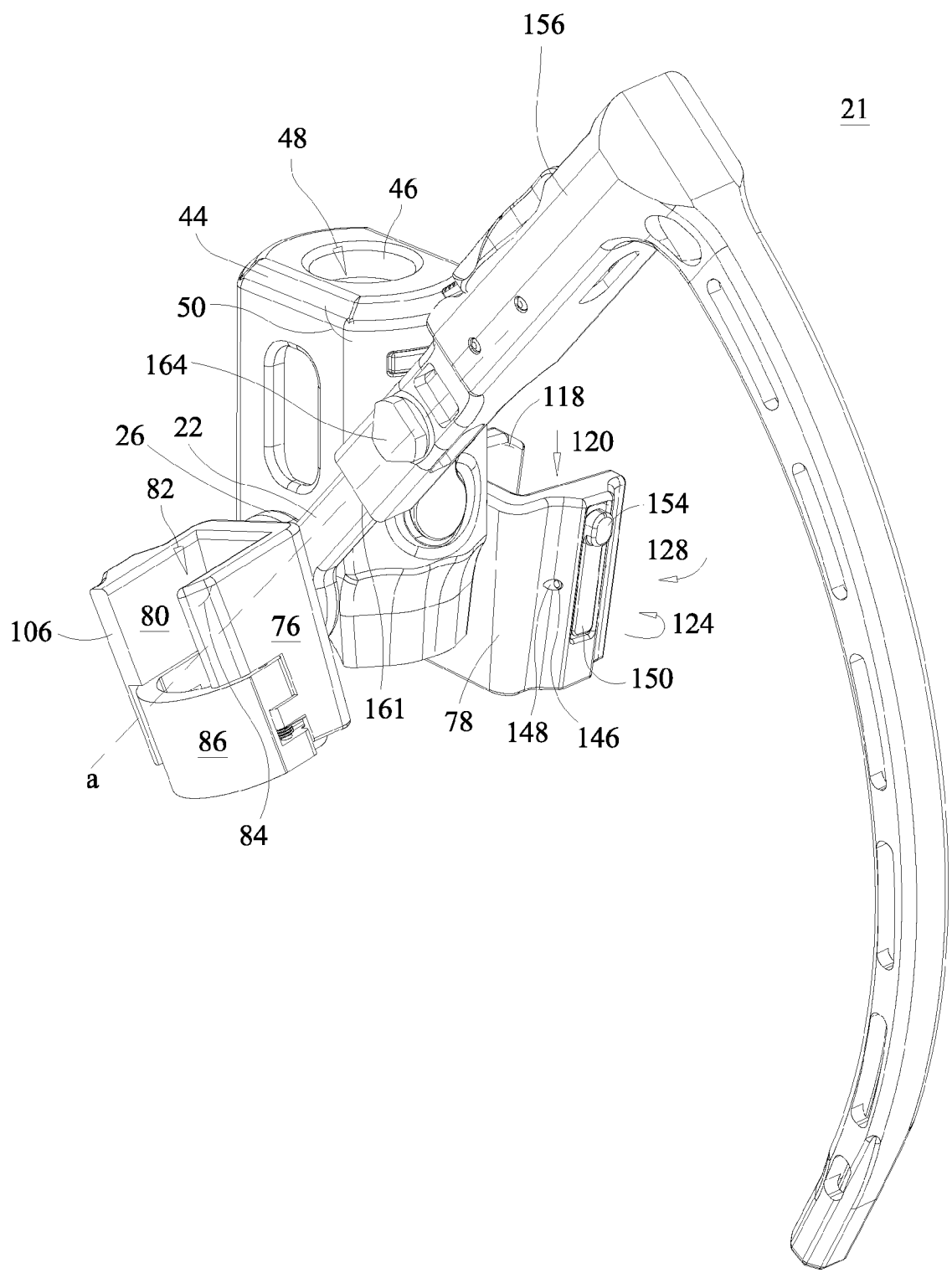
FIG. 2 is a perspective view of components of the system shown in FIG. 1.

Housing 44 is connected to at least one second body, such as, for example, housing 74. Housing 74 is configured for disposal of an extender 28 such that outer surface 30 of extender 28 that is disposed in housing 74 is spaced apart from outer surface 30 of extender 28 that is disposed in housing 44. In various embodiments, housing 74 includes a pair of second bodies, such as, for example, housing 76 and housing 78, as shown in FIG. 2. In some embodiments, housing 44 is disposed centrally relative to housing 76 and housing 78. In various embodiments, housing 44 and 74 or alternatively, housing 44, 76 and 78 are disposed in a serial configuration. In some embodiments, housing 44 is disposed intermediate to housing 76 and housing 78. In various embodiments, housing 74 is rotatable relative to housing 44 or alternatively, housings 76, 78 are rotatable relative to housing 44 via the rotation of end 26 of member 22.

Housing 76 includes an interior surface 80 that defines a passage 82 configured for engagement with outer surface 30 of extender 28. An exterior surface 84 defines the outer shape of housing 76. Housing 76 includes a capture element 86 configured to facilitate engagement and disengagement of extender 28 within housing 76. Capture element 86 extends between an end 88 and an end 90 and comprises an arcuate configuration. In some embodiments, capture element 86 is rotatable relative to housing 76. In various embodiments, capture element 86 connects at end 88 to housing 76 via a hinge 92.

Housing 76 includes a lock 94 that releasably engages capture element 86 with surface 84 of housing 76. Lock 94 includes a slot 96 at end 90 of capture element 86 and a latch 98. Latch 98 is disposed within a recess 100 defined by surface 84. Latch 98 extends between a proximal end 102 and a distal end 104. Latch 98 includes an opening 106. A pin 108 connects and facilitates movement of latch 98 within recess 100. Pin 108 is inserted into both an aperture 110 defined by surface 84 and opening 106. In some embodiments, aperture 110 can be an opening, hole, slot, orifice or slit.

Figure 6:
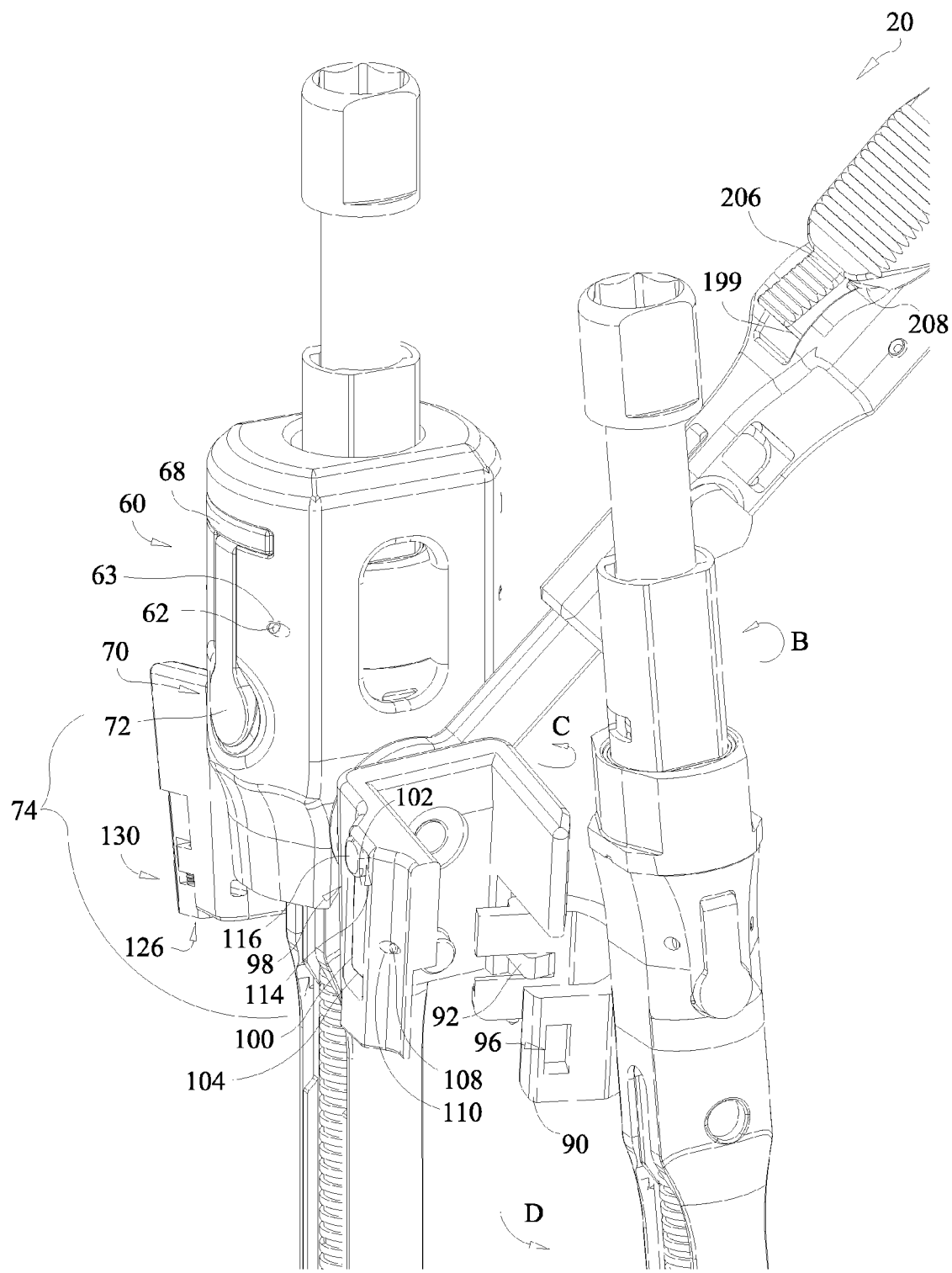
FIG. 6 is a breakaway view of components of the system shown in FIG. 1.
Figure 7:
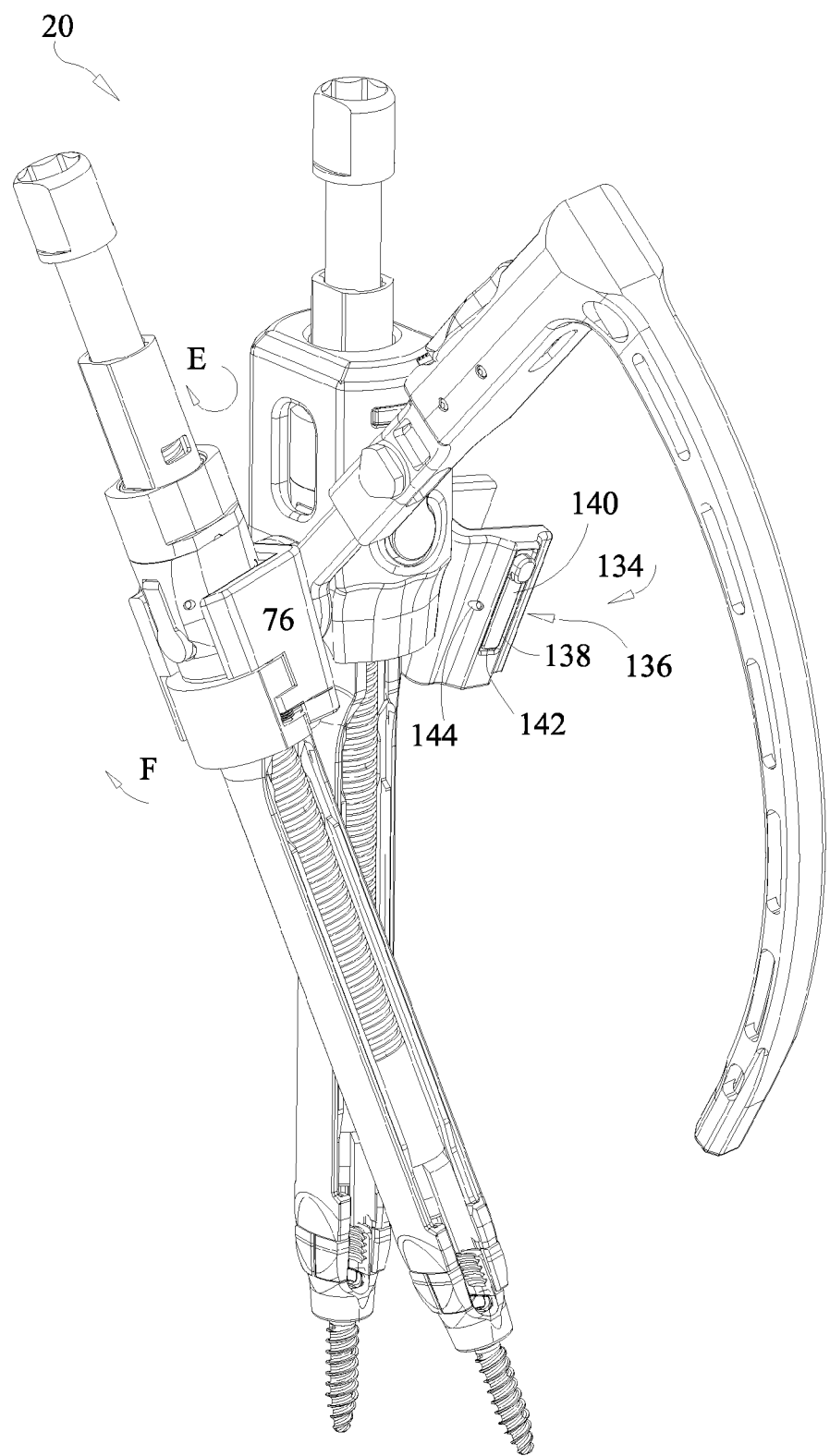
FIG. 7 is a perspective view of components of the system shown in FIG. 1.
Figure 8:
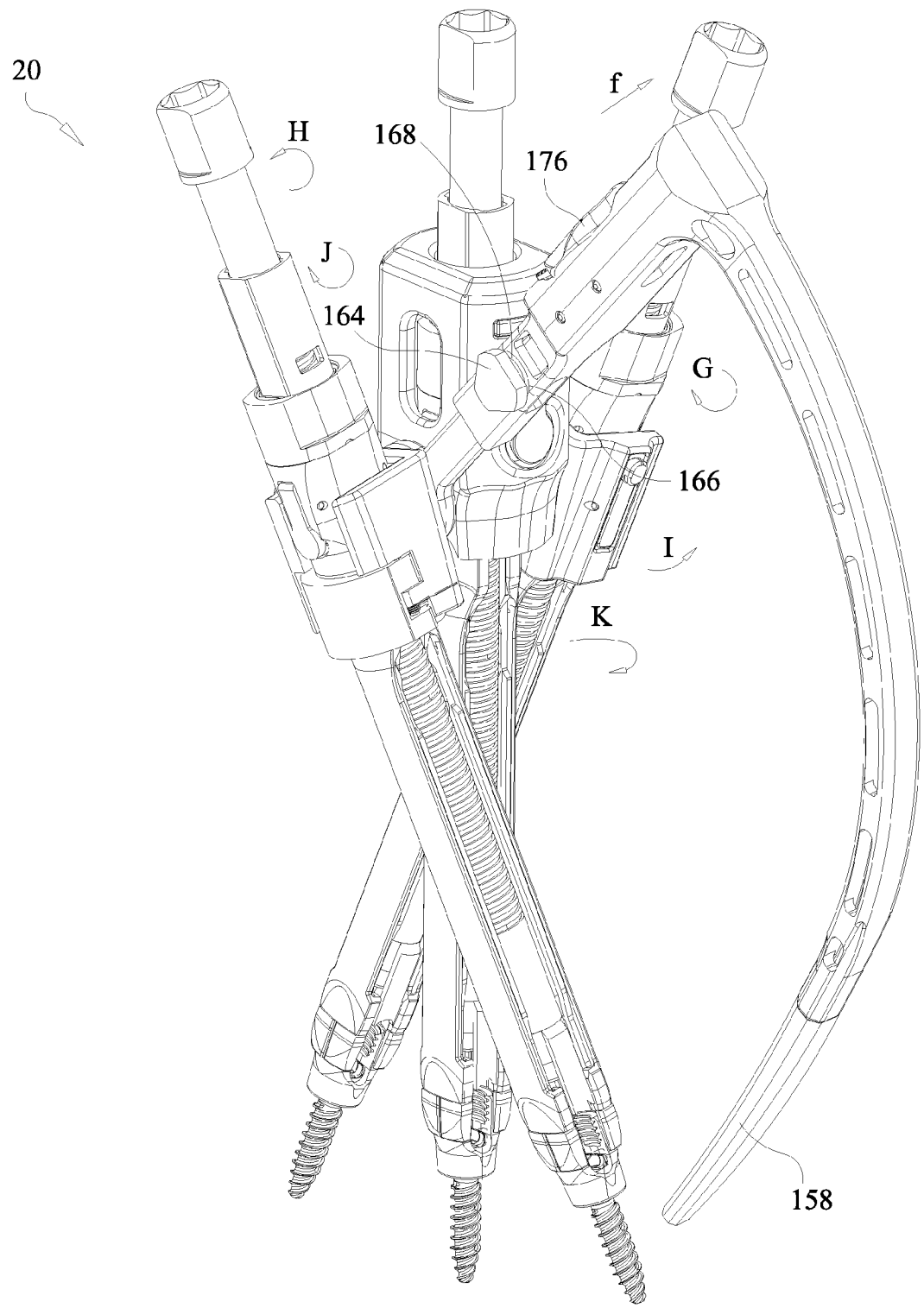
FIG. 8 is a perspective view of components of the system shown in FIG. 1.

End 104 includes a tab 112 that engages slot 96 to engage and disengage capture element 86 from housing 76. In one embodiment, end 102 engages a biasing member, such as, for example, a spring 114, as shown in FIG. 6. A button 116 is positioned on end 102. Button 116 is depressible and engages spring 114 causing tab 112 to engage slot 96 to either engage or disengage surface 30 of extender 28 to either lock or unlock extender 28 within passage 82.

Housing 78 includes an interior surface 118 that defines a passage 120 configured for engagement with outer surface 30 of extender 28. An exterior surface 122 defines the outer shape of housing 78. Housing 78 includes a capture element 124 configured to facilitate engagement and disengagement of extender 28 within housing 78. Capture element 124 extends between an end 126 and an end 128 and comprises an arcuate configuration. In some embodiments, capture element 124 is rotatable relative to housing 78. In various embodiments, capture element 124 connects at end 126 to housing 78 via a hinge 130.

Housing 78 includes a lock 132 that releasably engages capture element 124 with surface 122 of housing 78. Lock 132 includes a slot 134 at end 128 of capture element 124 and a latch 136. Latch 136 is disposed within a recess 138 defined by surface 122. Latch 136 extends between a proximal end 140 and a distal end 142. Latch 136 includes an opening 144. A pin 146 connects and facilitates movement of latch 136 within recess 138. Pin 146 is inserted into both an aperture 148 defined by surface 122 and opening 144. In some embodiments, aperture 148 can be an opening, hole, slot, orifice or slit.

Figure 4:
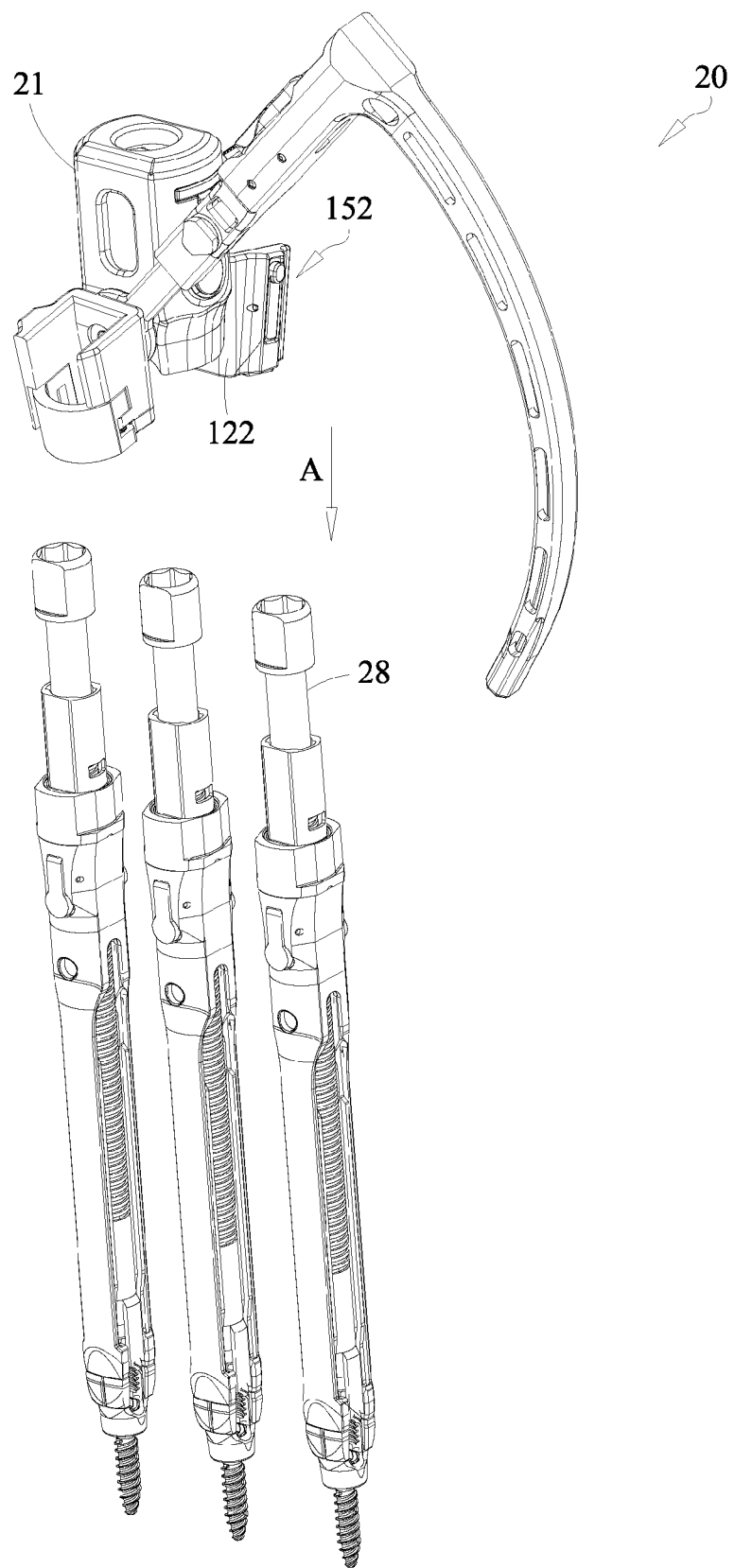
FIG. 4 is a perspective view of components of the system shown in FIG. 1.

End 142 includes a tab 150 that engages slot 134 to engage and disengage capture element 124 from housing 78. In one embodiment, end 140 engages a biasing member, such as, for example, a spring 152, as shown in FIG. 4. A button 154 is positioned on end 140. Button 154 is depressible and engages spring 152 causing tab 150 to engage slot 134 to either engage or disengage surface 30 of extender 28 to either lock or unlock extender 28 within passage 120.

Member 22 is connected with a second member 156. Member 156 is configured for engagement with a second implant, such as, for example, a spinal rod 158. In various embodiments, the cross-section of rod 158 may have various configurations, for example, round, oval, rectangular, polygonal, irregular, tapered, offset, staggered, uniform and non-uniform.

Member 156 is rotatable relative to the housings to dispose rod 158 with extenders 28 and to place rod 158 in alignment with one or more bone fasteners 36. Member 156 has an arcuate configuration and extends between an end 160 and an end 162. End 160 is connected to member 22 via a slot 161 at end 160 and a tensioning member, such as, for example, a clamp 164. Clamp 164 is configured for rotation and engagement within a transverse opening 166 at end 160 and a transverse opening 168 disposed at end 24 of member 22. In some embodiments, openings 166, 168 are threaded. Clamp 164 is transversely oriented within openings 166, 168. Clamp 164 extends between an end 170 and an end 172. End 170 includes a threaded portion that is configured for threaded engagement with openings 166, 168. End 172 includes a thumbwheel 174. Thumbwheel 174 facilitates rotation of clamp 164 within openings 166, 168 to engage member 156 with member 22. In various embodiments, member 22 includes a plurality of transverse openings 168 such that the length of member 22 can be selectively adjusted.

End 162 is connected to an end of rod 158. A lock 176 is disposed in a recess 178 located at end 160 and is configured to releasably engage rod 158 with member 156. Lock 176 is adjustable in a configuration to selectively apply a force, in the direction shown by arrow f in FIG. 8, to rod 158 for engagement. Lock 176 includes a lever 180, a biasing member 182 and a collet 184. Lever 180 includes an end 186 and an end 188. End 186 engages a portion 190 of biasing member 182 via a hinge 192. Biasing member 182 engages collet 184 with a portion 194 to selectively open and close collet 184, thereby releasably engaging rod 158.

A lock 196 comprising a safety latch 198 is disposed with recess 178 and is configured for engagement with lever 180 of lock 176. A pin 200 is disposed within a transverse opening 202 defined within recess 178 and is disposed within a transverse opening 204 defined by latch 198. In one embodiment, a resiliently biased member, such as, for example, a spring 199 is disposed under latch 198. An end 206 of latch 198 engages a groove 208 disposed at end 188 of lever 180.

When lock 196 is translated in a distal direction, end 206 of latch 198 disengages from groove 208 of lever 180. Lever 180 is pulled and rotated in a clockwise direction, translating biasing member 182 in a distal direction, opening collet 184. Rod 158 is inserted into end 162 and lever 180 is pushed in a counterclockwise direction, translating biasing member 182 in a proximal direction, closing collet 184 such that rod 158 engages with end 162. Lock 196 is translated in a proximal direction and engages with groove 208.

In some embodiments, spinal implant system 20 delivers a spinal implant to a surgical site by attaching extenders to the instrument in a manner that separates and spaces apart the extenders such that the extenders do not mate together. In some embodiments, the instrument allows a medical practitioner to easily engage and disengage extenders from the device without having to remove all of the extenders at once.

Figure 3:
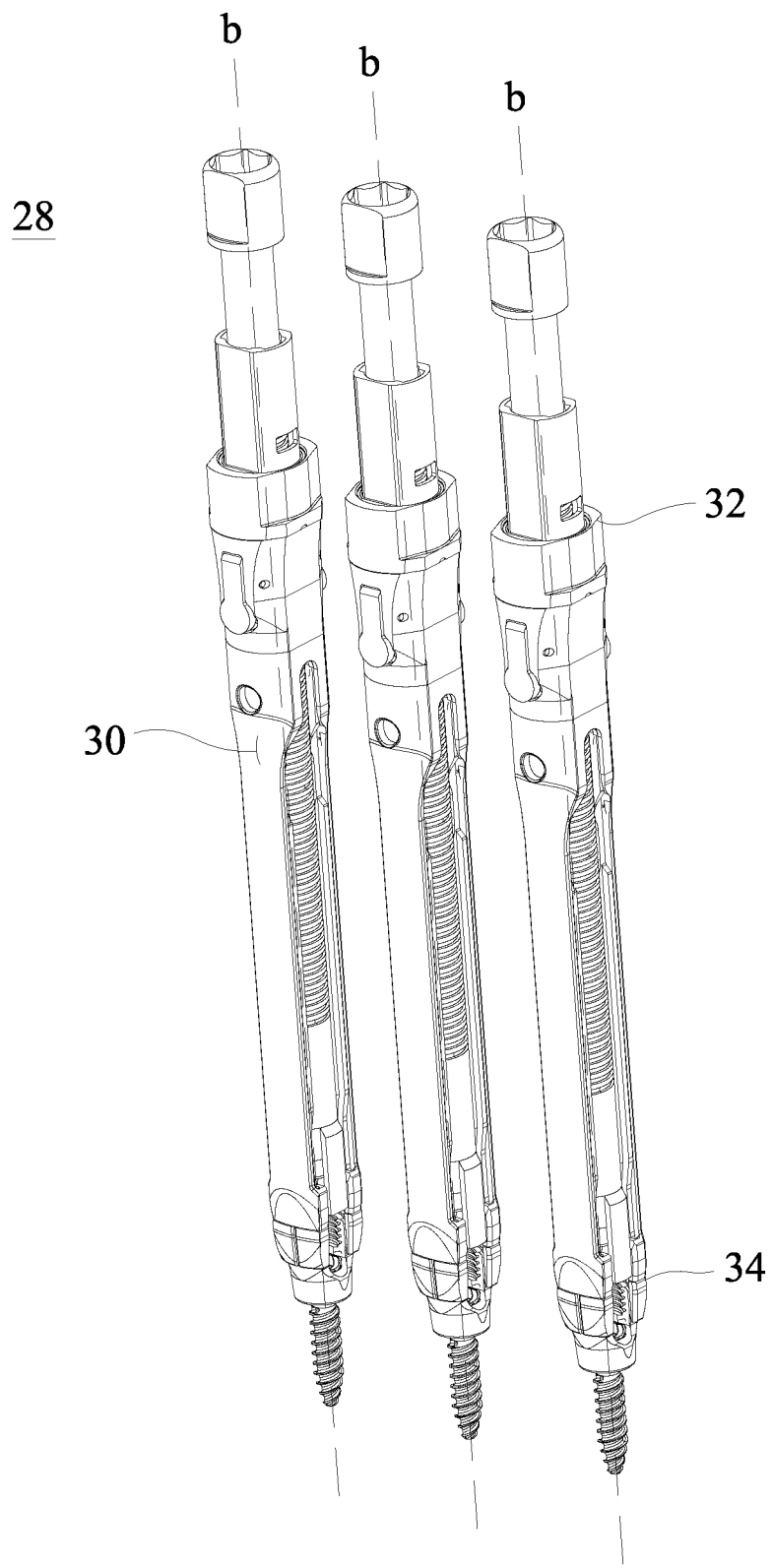
FIG. 3 is a perspective view of components of the system shown in FIG. 1.
Figure 5:
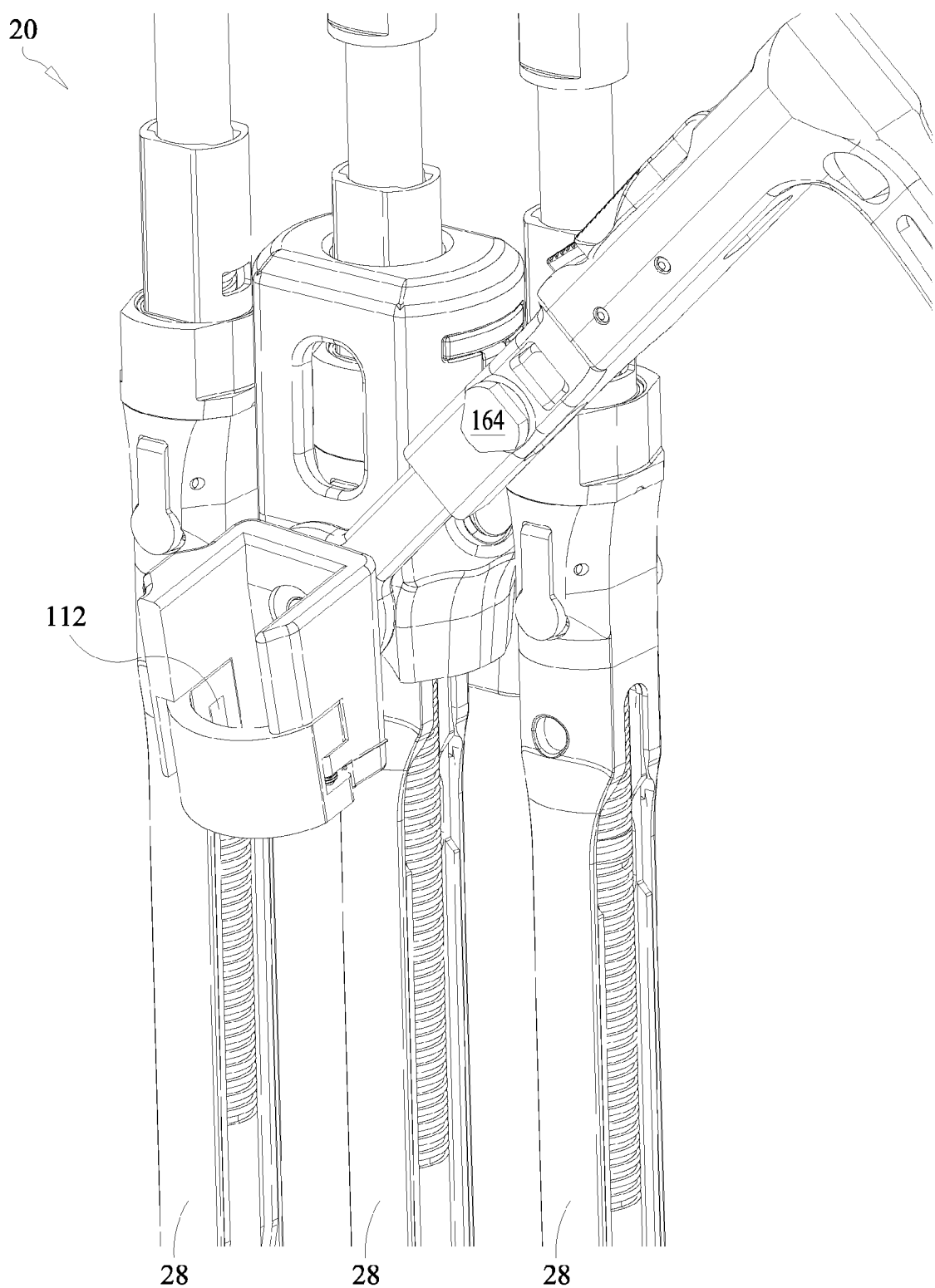
FIG. 5 is a breakaway view of components of the system shown in FIG. 1.

In operation, extenders 28 are connected with receiver 38 of each bone fastener 36 at end 34, as shown in FIG. 3. Fasteners 36 are affixed with vertebrae. Central housing 44 is translated, such as, for example, in a distal direction shown by arrow A in FIG. 4, onto central extender 28, as shown in FIG. 5. Button 72 of latch 66 is depressed and engages spring 70, causing prong 64 to engage latch 54, engaging and locking surface 30 of central extender 28 within passage 48.

Housing 76, disposed laterally relative to central body 44, is positioned adjacent extender 28, which is disposed laterally relative to central extender 28. Extender 28 is rotated in a direction, such as, for example, a counterclockwise direction, as shown by arrow B in FIG. 6. Button 116 of latch 98 is depressed and tab 112 disengages with slot 96. Hinge 96 rotates end 88 of capture element 86 in a direction, such as, for example, a counterclockwise direction, as shown by arrow C, which moves capture element 86 in a direction, such as, for example, an outward direction, as shown by arrow D. Extender 28 is inserted into housing 76 and hinge 96 rotates end 88 of capture element 86 in a direction, such as, for example, a clockwise direction, as shown by arrow E in FIG. 7, which moves capture element 86 in a direction, such as, for example, an inward direction, as shown by arrow F. Slot 96 engages tab 112 and an audible click is provided.

Housing 78, disposed laterally relative to central body 44, is positioned adjacent extender 28, which is disposed laterally relative to central extender 28. Extender 28 is rotated in a direction, such as, for example, a clockwise direction, as shown by arrow G in FIG. 8. Button 154 of latch 136 is depressed and tab 150 disengages with slot 134. Hinge 130 rotates end 126 of capture element 124 in a direction, such as, for example, a counterclockwise direction, as shown by arrow H, which moves capture element 124 in a direction, such as, for example, an outward direction, as shown by arrow I. Extender 28 is inserted into housing 78 and hinge 130 rotates end 126 of capture element 124 in a direction, such as, for example, a clockwise direction, as shown by arrow J, which moves capture element 124 in a direction, such as, for example, an inward direction, as shown by arrow K. Slot 134 engages tab 150 and an audible click is provided.

Figure 9:
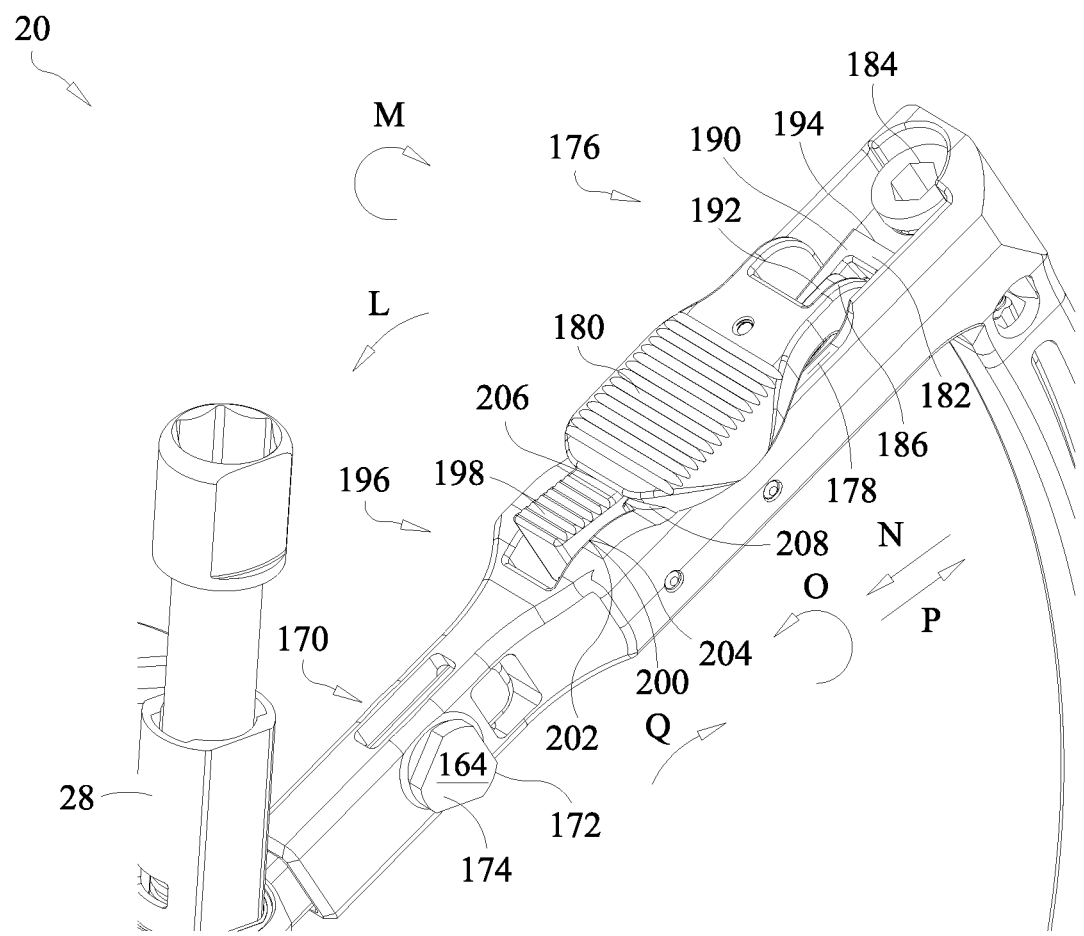
FIG. 9 is a breakaway view of components of the system shown in FIG. 1.

Lock 196 is rotated in a direction, as shown by arrow L in FIG. 9. End 206 of latch 198 disengages from groove 208 of lever 180. Lever 180 is manipulated and rotated in a direction, such as, for example, a clockwise direction, as shown by arrow M, translating biasing member 182 in a direction, such as, for example, a distal direction as shown by arrow N, opening collet 184. Rod 158 is inserted into end 162 and lever 180 is pushed and rotated in a direction, such as, for example, counterclockwise direction as shown by arrow O, translating biasing member 182 in a direction, such as, for example, a proximal direction as shown by arrow P, closing collet 184 such that rod 158 engages end 162. Lock 196 translates, in a direction shown by arrow Q, and engages groove 208.

In assembly, operation and use, spinal implant system 20, similar to the systems described herein, is employed with a surgical procedure for treatment of a spinal disorder affecting a section of a spine of a patient, as discussed herein. Spinal implant system 20 may also be employed with other surgical procedures. For example, spinal implant system 20 can be used with a surgical procedure for treatment of a condition or injury of an affected section of the spine including vertebrae V.

Figure 10:
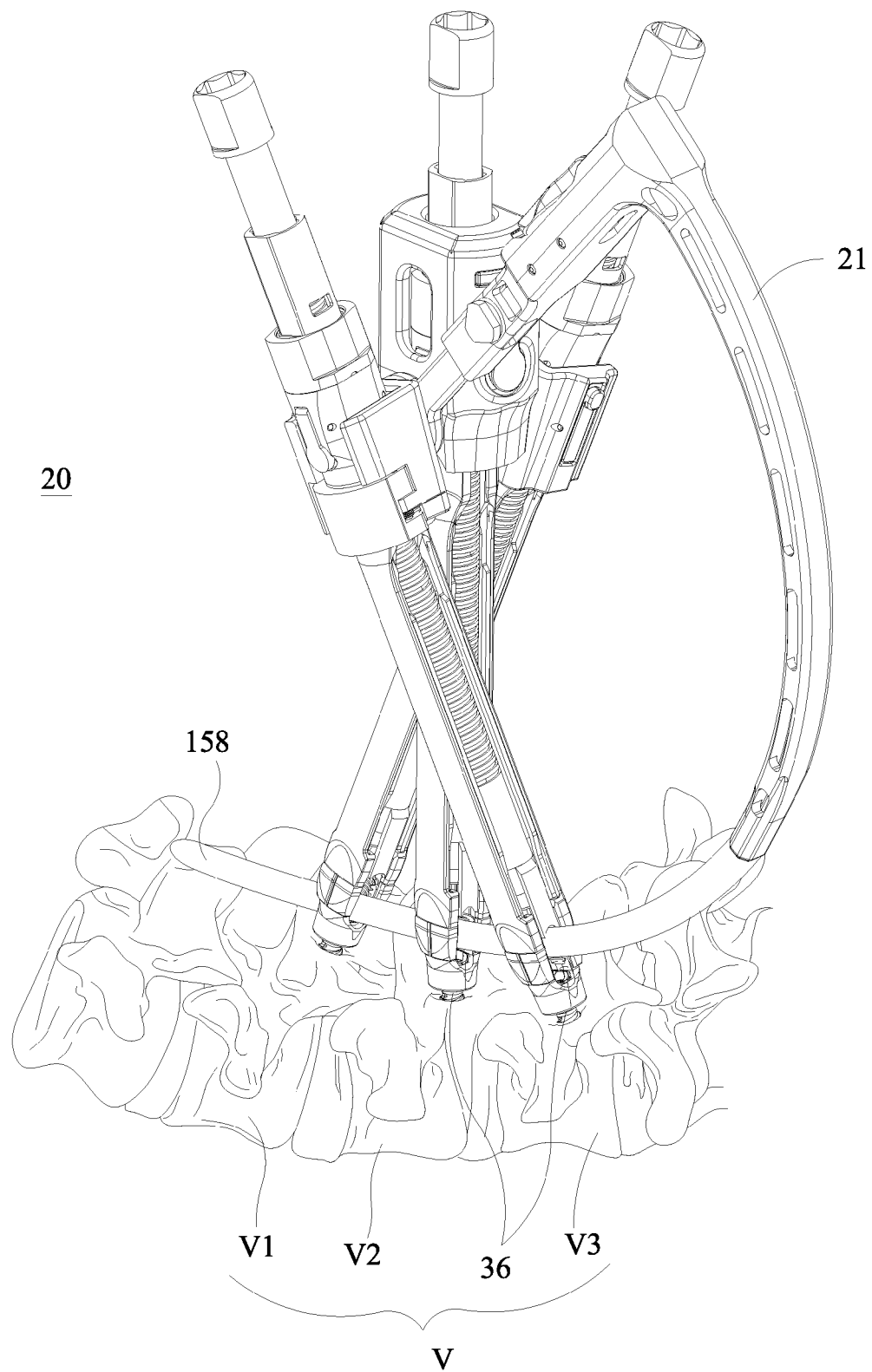
FIG. 10 is a perspective view of components of the system shown in FIG. 1 disposed with vertebrae.

In use, to treat the affected section of vertebrae V, a medical practitioner obtains access to a surgical site including vertebrae V1, V2, V3, as shown in FIG. 10, in any appropriate manner, such as through incision and retraction of tissues. In some embodiments, spinal implant system 20 may be used in any existing surgical method or technique including open surgery, mini-open surgery, minimally invasive surgery, including percutaneous surgical implantation, whereby vertebrae is accessed through a micro-incision, or sleeve that provides a protected passageway to the area. Once access to the surgical site is obtained, the particular surgical procedure is performed for treating the spinal disorder. Spinal implant system 20 is employed to augment the surgical treatment. Spinal implant system 20 can be delivered or implanted as a pre-assembled device or can be assembled in situ. Spinal implant system 20 may be completely or partially revised, removed or replaced, for example, removing instrument 21 and/or extenders 28, rod 158 and/or one or all of the components of spinal implant system 20 before, during or after the surgical procedure.

Pilot holes or the like are made in vertebrae V1, V2, V3 for receiving shaft 40 of each of bone fasteners 36. Spinal implant system 20 is disposed adjacent vertebrae V at a surgical site and the components of spinal implant system 20 are manipulable to drive, torque, insert or otherwise connect bone fasteners 36 to vertebrae and/or dispose a vertebral construct, such as, for example, rod 158 with bone fasteners 36.

The medical practitioner introduces extenders 28 for connection with receiver 38 of each bone fastener 36 at end 34, as shown in FIG. 3. Fasteners 36 are affixed with vertebrae V1-V3. Central housing 44 is translated in a distal direction shown by arrow A in FIG. 4, onto central extender 28, as shown in FIG. 5. Button 72 of latch 66 is depressed and engages spring 70, causing prong 64 to engage latch 54, engaging and locking surface 30 of central extender 28 within passage 48. Housing 76, disposed laterally relative to central housing 44, is positioned adjacent extender 28, which is disposed laterally relative to central extender 28. Extender 28 is rotated in a counterclockwise direction, as shown by arrow B in FIG. 6. Button 116 of latch 98 is depressed and tab 112 disengages slot 96. Hinge 96 rotates end 88 of capture element 86 in a counterclockwise direction, as shown by arrow C, which moves capture element 86 in an outward direction, as shown by arrow D. Extender 28 is inserted into housing 76 and hinge 96 rotates end 88 of capture element 86 in a clockwise direction, as shown by arrow E in FIG. 7, which moves capture element 86 in an inward direction, as shown by arrow F. Slot 96 engages tab 112 and an audible click is provided.

Housing 78, disposed laterally relative to central housing 44 is positioned adjacent extender 28, which is disposed laterally relative to central extender 28. Extender 28 is rotated in a clockwise direction, as shown by arrow G in FIG. 8. Button 154 of latch 136 is depressed and tab 150 disengages slot 134. Hinge 130 rotates end 126 of capture element 124 in a counterclockwise direction, as shown by arrow H, which moves capture element 124 in an outward direction, as shown by arrow I. Extender 28 is inserted into housing 78 and hinge 130 rotates end 126 of capture element 124 in a clockwise direction, as shown by arrow J, which moves capture element 124 in an inward direction, as shown by arrow K. Slot 134 engages tab 150 and an audible click is provided.

Lock 196 rotates, as shown by arrow L in FIG. 9. End 206 of latch 198 disengages from groove 208 of lever 180. Lever 180 is rotated in a clockwise direction as shown by arrow M, translating biasing member 182 in a distal direction as shown by arrow N, opening collet 184. Rod 158 is inserted into end 162 and lever 180 is rotated in a counterclockwise direction as shown by arrow O, translating biasing member 182 in a proximal direction as shown by arrow P, closing collet 184 such that rod 158 engages end 162. Lock 196 is rotated in direction shown by arrow Q, and engages groove 208. Member 156 is rotatable relative to member 22 and/or one or more of housings 44, 76, 78, to dispose rod 158 with extenders 28 and to place rod 158 in alignment with one or more bone fasteners 36. Instrument 21 aligns and disposes rod 158 with bone fasteners 36.

In one embodiment, upon completion of the procedure, the surgical instruments, assemblies and non-implanted components of system 20 are removed from the surgical site and the incision(s) is closed.

In some embodiments, rod 158 and/or one or more of fasteners 36 may be engaged with tissue in various orientations, such as, for example, series, parallel, offset, staggered and/or alternate vertebral levels. In some embodiments, one or more of fasteners 36 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, bone fasteners 36 and/or rod 158 may be coated with an osteoconductive material such as hydroxyapatite and/or osteoinductive agent such as a bone morphogenic protein for enhanced bony fixation. In some embodiments, bone fasteners 36 and/or rod 158 may be coated with therapeutic and/or pharmacological agents for release, including sustained release, to treat, for example, pain, inflammation and degeneration.

One or more of the components of spinal implant system 20 can be made of radiolucent materials such as polymers. Radiomarkers may be included for identification under x-ray, fluoroscopy, CT or other imaging techniques. Metallic or ceramic radiomarkers, such as tantalum beads, tantalum pins, titanium pins, titanium endcaps, and platinum wires can be used. In some embodiments, the use of surgical navigation, microsurgical and image guided technologies may be employed to access, view and repair spinal deterioration or damage, with the aid of spinal implant system 20. In some embodiments, spinal implant system 20 may include one or a plurality of plates, connectors and/or bone fasteners for use with a single vertebral level or a plurality of vertebral levels.

In one embodiment, spinal implant system 20 includes an agent, which may be disposed, packed, coated or layered within, on or about the components and/or surfaces of spinal implant system 20. In some embodiments, the agent may include bone growth promoting material, such as, for example, bone graft to enhance fixation of the components and/or surfaces of spinal implant system 20 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member including a first body connected to a pair of second bodies, the first body being configured for disposal of an implant support having an outer surface and at least one of the second bodies including a capture element configured to dispose an implant support having an outer surface with the at least one of the second bodies such that the outer surfaces are spaced apart and each of the implant supports are engageable with a first implant, the first member comprising an elongated member having an end that engages the first body, the end being positioned between the first body and one of the second bodies such that the end engages one of the second bodies; and
   a second member connected with the first member and engageable with a second implant,
   wherein the members are relatively movable to dispose the second implant with the implant supports and in alignment with at least one of the first implants.

2. A surgical instrument as recited in claim 1, wherein the bodies are disposed in a serial configuration.

3. A surgical instrument as recited in claim 1, wherein the end engages one of the second bodies in a manner that allows the first body and one of the second bodies to pivot relative to the elongated member.

4. A surgical instrument as recited in claim 1, wherein the first body includes a lock such that an implant support is releasably engageable with the first body.

5. A surgical instrument as recited in claim 1, wherein the second bodies are rotatable relative to the first body.

6. A surgical instrument as recited in claim 1, wherein the capture element is rotatable relative to the at least one of the second bodies.

7. A surgical instrument as recited in claim 1, wherein the capture element is connected to the at least one of the second bodies via a hinge.

8. A surgical instrument as recited in claim 1, wherein the capture element includes an arcuate configuration.

9. A surgical instrument as recited in claim 1, wherein the at least one of the second bodies includes a lock such that the capture element includes an end that is releasably engageable with the at least one of the second bodies.

10. A surgical instrument as recited in claim 1, wherein the elongated member includes a linear configuration and defines a longitudinal axis extending from the end to an opposite second end, the second end being positioned within the second member.

11. A surgical instrument as recited in claim 1, wherein the second member includes an arcuate configuration and extends between a first end connected with the first member and a second end connected with the second implant.

12. A surgical instrument as recited in claim 1, wherein the second member includes a first lock such that the second implant is releasably engageable with the second member.

13. A surgical instrument as recited in claim 12, wherein the first lock is adjustable in a configuration to selectively apply a force to the second implant for engagement therewith.

14. A surgical instrument as recited in claim 12, wherein the second member further includes a second lock and the first lock is movable between a locked position and a non-locking position, the second lock resisting movement of the first lock from the locked position.

15. A surgical instrument as recited in claim 1, wherein the second member is rotatable relative to the bodies to dispose the second implant with the implant supports and in alignment with at least one of the first implants.

16. A surgical instrument comprising:
a first member including a first body connected to a pair of second bodies, the first body being disposed intermediate to the second bodies, the first body being configured for disposal of an extender having an outer surface, each of the second bodies including a capture element that is rotatable relative to the second body and is configured to dispose an extender having an outer surface with the second body such that the outer surfaces are spaced apart and each of the extenders are engageable with a bone fastener, the first member comprising an elongated member having an end that is positioned between the first body and one of the second bodies such that the end engages the first body and one of the second bodies; and
a second member connected with the first member and including a first lock that is releasably engageable with a spinal rod,
wherein the members are relatively movable and the second member is rotatable relative to the bodies to dispose the spinal rod with the extenders and in alignment with at least one of the bone fasteners.

17. A surgical instrument as recited in claim 16, wherein the first body includes a lock such that an extender is releasably engageable with the first body.

18. A surgical instrument as recited in claim 16, wherein each of the second bodies is rotatable relative to the first body.

19. A surgical system comprising:
a plurality of extenders;
a plurality of bone fasteners, wherein each extender is engageable with a bone fastener;
a spinal rod; and
a surgical instrument comprising a first member including a first body connected to at least one second body, the first body being configured for disposal of an extender having an outer surface and the at least one second body including a capture element configured to dispose an extender having an outer surface with the at least one second body such that the outer surfaces are spaced apart, and a second member connected with the first member and engageable with the spinal rod, wherein the members are relatively movable to dispose the spinal rod with the extenders and in alignment with at least one of the bone fasteners, and wherein the first member comprises an elongated member having an end that is positioned between the first body and the at least one second body such that the end engages the first body and the at least one second body.

* * * * *